(12) United States Patent
Iddan

(10) Patent No.: US 8,702,597 B2
(45) Date of Patent: Apr. 22, 2014

(54) IMMOBILIZABLE IN-VIVO IMAGER WITH MOVEABLE FOCUSING MECHANISM

(75) Inventor: Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 1244 days.

(21) Appl. No.: 11/025,124

(22) Filed: Dec. 30, 2004

(65) Prior Publication Data

US 2005/0143624 A1 Jun. 30, 2005

Related U.S. Application Data

(60) Provisional application No. 60/533,264, filed on Dec. 31, 2003.

(51) Int. Cl.
*A61B 1/06* (2006.01)

(52) U.S. Cl.
USPC ............ 600/167; 600/168; 600/171; 600/173

(58) Field of Classification Search
USPC .................................. 600/101, 109, 167, 173
See application file for complete search history.

(56) References Cited

U.S. PATENT DOCUMENTS

| | | | |
|---|---|---|---|
| 3,190,286 A | 6/1965 | Stokes | |
| 3,528,429 A | 9/1970 | Beal et al. | |
| 3,643,653 A * | 2/1972 | Takahashi et al. | ............ 600/129 |
| 3,683,389 A | 8/1972 | Hollis | |
| 3,719,183 A | 3/1973 | Schwartz | |
| 3,888,237 A | 6/1975 | Mori | |
| 3,971,362 A | 7/1976 | Pope et al. | |
| 4,040,413 A | 8/1977 | Ohshiro | |
| 4,083,369 A | 4/1978 | Sinnreich | |
| 4,148,307 A | 4/1979 | Utsugi | |
| 4,176,662 A | 12/1979 | Frazer | |
| 4,217,045 A | 8/1980 | Ziskind | |
| 4,278,077 A | 7/1981 | Mizumoto | |
| 4,389,208 A | 6/1983 | LeVeen et al. | |
| 4,425,117 A | 1/1984 | Hugemann et al. | |
| 4,456,011 A | 6/1984 | Warnecke | |
| 4,677,967 A | 7/1987 | Zartman | |
| 4,689,621 A | 8/1987 | Kleinberg | |
| 4,741,327 A | 5/1988 | Yabe | |

(Continued)

FOREIGN PATENT DOCUMENTS

| | | |
|---|---|---|
| DE | 34 40 177 | 5/1986 |
| EP | 0967656 A2 | 12/1999 |

(Continued)

OTHER PUBLICATIONS

U.S. Appl. No. 60/801,387, filed May 19, 2006, Swain et al.

(Continued)

*Primary Examiner* — Matthew J Kasztejna

(74) *Attorney, Agent, or Firm* — Pearl Cohen Zedek Latzer Baratz LLP

(57) ABSTRACT

A system, method and device for immobilizing an imager in-vivo and/or focusing images on the imager reflected from an in-vivo site to be monitored with for example a moveable or otherwise adjustable focusing mechanism. The imaging sensor may for example be positioned on an acute angle to an in-vivo surface to which the device is immobilized so that the device may for example image an in-vivo area that is opposed to such device. Sensors in addition to or other than an imaging sensor may be used.

12 Claims, 3 Drawing Sheets

(56) References Cited

U.S. PATENT DOCUMENTS

| | | | | |
|---|---|---|---|---|
| 4,832,003 A | | 5/1989 | Yabe | |
| 4,844,076 A | | 7/1989 | Lesho et al. | |
| 4,878,898 A | | 11/1989 | Griffin et al. | |
| 4,890,159 A | | 12/1989 | Ogiu | |
| 4,915,113 A | | 4/1990 | Holman | |
| 4,929,214 A | | 5/1990 | Liebermann | |
| 4,936,823 A | | 6/1990 | Colvin et al. | |
| 5,108,407 A | | 4/1992 | Geremia et al. | |
| 5,191,879 A | * | 3/1993 | Krauter | 600/109 |
| 5,195,955 A | | 3/1993 | Don Michael | |
| 5,279,607 A | | 1/1994 | Schentag et al. | |
| 5,318,589 A | | 6/1994 | Lichtman | |
| 5,337,732 A | | 8/1994 | Grundfest et al. | |
| 5,421,337 A | | 6/1995 | Richards-Kortum et al. | |
| 5,495,114 A | | 2/1996 | Adair | |
| 5,553,741 A | | 9/1996 | Sancoff et al. | |
| 5,554,914 A | | 9/1996 | Miyazawa | |
| 5,575,754 A | * | 11/1996 | Konomura | 600/117 |
| 5,595,565 A | | 1/1997 | Treat et al. | |
| 5,604,531 A | | 2/1997 | Iddan et al. | |
| 5,662,587 A | | 9/1997 | Grundfest et al. | |
| 5,723,844 A | | 3/1998 | Dow et al. | |
| 5,734,418 A | | 3/1998 | Danna | |
| 5,754,313 A | | 5/1998 | Pelchy et al. | |
| 5,782,771 A | | 7/1998 | Hussman | |
| 5,797,837 A | | 8/1998 | Minami | |
| 5,819,736 A | | 10/1998 | Avny et al. | |
| 5,830,217 A | | 11/1998 | Ryan | |
| 5,833,603 A | | 11/1998 | Kovacs et al. | |
| 5,853,005 A | | 12/1998 | Scanlon | |
| 5,895,350 A | * | 4/1999 | Hori | 600/167 |
| 5,904,647 A | | 5/1999 | Ouchi | |
| 5,929,901 A | | 7/1999 | Adair et al. | |
| 5,938,585 A | * | 8/1999 | Donofrio | 600/115 |
| 5,947,924 A | | 9/1999 | Liprie | |
| 5,980,453 A | | 11/1999 | Forkey et al. | |
| 5,984,860 A | | 11/1999 | Shan | |
| 5,986,693 A | | 11/1999 | Adair et al. | |
| 5,993,378 A | | 11/1999 | Lemelson | |
| 6,007,482 A | | 12/1999 | Madni et al. | |
| 6,010,453 A | | 1/2000 | Finddian-Green | |
| 6,019,721 A | * | 2/2000 | Holmes et al. | 600/167 |
| 6,043,839 A | | 3/2000 | Adair et al. | |
| 6,074,349 A | | 6/2000 | Crowley | |
| 6,114,037 A | | 9/2000 | Vos et al. | |
| 6,162,171 A | | 12/2000 | Ng et al. | |
| 6,165,128 A | | 12/2000 | Cespedes et al. | |
| 6,204,524 B1 | | 3/2001 | Rhodes | |
| 6,222,620 B1 | | 4/2001 | Jung et al. | |
| 6,240,312 B1 | | 5/2001 | Alfano et al. | |
| 6,251,093 B1 | | 6/2001 | Valley et al. | |
| 6,266,550 B1 | | 7/2001 | Selmon et al. | |
| 6,285,897 B1 | | 9/2001 | Kilcoyne et al. | |
| 6,338,709 B1 | | 1/2002 | Geoffrion et al. | |
| 6,364,830 B1 | * | 4/2002 | Durell | 600/173 |
| 6,402,686 B1 | | 6/2002 | Ouchi | |
| 6,458,074 B1 | | 10/2002 | Matsui et al. | |
| 6,471,631 B1 | | 10/2002 | Slater et al. | |
| 6,475,145 B1 | | 11/2002 | Baylor | |
| 6,527,753 B2 | | 3/2003 | Sekine et al. | |
| 6,535,764 B2 | | 3/2003 | Imran et al. | |
| 6,549,796 B2 | | 4/2003 | Sohrad | |
| 6,579,311 B1 | | 6/2003 | Makower | |
| 6,612,982 B1 | | 9/2003 | Ouchi | |
| 6,632,175 B1 | | 10/2003 | Marshall | |
| 6,648,814 B2 | | 11/2003 | Kim et al. | |
| 6,689,056 B1 | | 2/2004 | Kilcoyne et al. | |
| 6,692,432 B1 | * | 2/2004 | Yarush et al. | 600/179 |
| 6,702,734 B2 | | 3/2004 | Kim et al. | |
| 6,709,387 B1 | | 3/2004 | Glukhovsky et al. | |
| 6,719,684 B2 | * | 4/2004 | Kim et al. | 600/101 |
| 6,783,499 B2 | | 8/2004 | Schwartz | |
| 6,929,636 B1 | | 8/2005 | von Alten | |
| 6,951,536 B2 | * | 10/2005 | Yokoi et al. | 600/128 |
| 6,979,290 B2 | * | 12/2005 | Mourlas et al. | 600/115 |
| 7,009,634 B2 | | 3/2006 | Iddan et al. | |
| 7,044,908 B1 | * | 5/2006 | Montalbo et al. | 600/160 |
| 7,066,879 B2 | * | 6/2006 | Fowler et al. | 600/102 |
| 7,066,880 B2 | * | 6/2006 | Wendlandt | 600/114 |
| 7,076,305 B2 | | 7/2006 | Imran et al. | |
| 7,107,100 B2 | | 9/2006 | Imran et al. | |
| 7,122,001 B2 | * | 10/2006 | Uchiyama et al. | 600/103 |
| 7,160,258 B2 | | 1/2007 | Imran et al. | |
| 7,175,593 B2 | * | 2/2007 | Durell | 600/173 |
| 7,261,728 B2 | | 8/2007 | Long et al. | |
| 7,509,174 B2 | | 3/2009 | Imran et al. | |
| 2001/0035902 A1 | | 11/2001 | Iddan et al. | |
| 2001/0049497 A1 | | 12/2001 | Kalloo et al. | |
| 2001/0051766 A1 | | 12/2001 | Gazdzinski | |
| 2002/0042562 A1 | | 4/2002 | Meron et al. | |
| 2002/0103417 A1 | | 8/2002 | Gazdzinski | |
| 2002/0109774 A1 | | 8/2002 | Meron et al. | |
| 2002/0138009 A1 | | 9/2002 | Brockway et al. | |
| 2002/0156347 A1 | | 10/2002 | Kim et al. | |
| 2002/0198439 A1 | | 12/2002 | Mizuno | |
| 2002/0198470 A1 | | 12/2002 | Imran et al. | |
| 2003/0013370 A1 | | 1/2003 | Glukhovsky | |
| 2003/0020810 A1 | * | 1/2003 | Takizawa et al. | 348/68 |
| 2003/0023150 A1 | * | 1/2003 | Yokoi et al. | 600/300 |
| 2003/0028078 A1 | | 2/2003 | Glukhovsky | |
| 2003/0092964 A1 | | 5/2003 | Kim et al. | |
| 2003/0117491 A1 | * | 6/2003 | Avni et al. | 348/77 |
| 2003/0130562 A1 | * | 7/2003 | Barbato et al. | 600/109 |
| 2003/0167000 A1 | * | 9/2003 | Mullick et al. | 600/424 |
| 2003/0167024 A1 | | 9/2003 | Imran et al. | |
| 2003/0214726 A1 | | 11/2003 | Mihara | |
| 2003/0216622 A1 | | 11/2003 | Meron et al. | |
| 2004/0073087 A1 | * | 4/2004 | Glukhovsky et al. | 600/109 |
| 2004/0092825 A1 | * | 5/2004 | Madar et al. | 600/473 |
| 2004/0097791 A1 | * | 5/2004 | Tokuda et al. | 600/173 |
| 2004/0133076 A1 | * | 7/2004 | Kobayashi et al. | 600/175 |
| 2004/0153008 A1 | | 8/2004 | Sharf et al. | |
| 2004/0176664 A1 | * | 9/2004 | Iddan | 600/160 |
| 2004/0186349 A1 | * | 9/2004 | Ewers et al. | 600/114 |
| 2004/0225189 A1 | * | 11/2004 | Kimoto et al. | 600/160 |
| 2005/0143623 A1 | | 6/2005 | Kojima | |
| 2005/0259487 A1 | | 11/2005 | Glukhovsky | |
| 2006/0004255 A1 | * | 1/2006 | Iddan et al. | 600/160 |
| 2006/0167339 A1 | | 7/2006 | Gilad et al. | |
| 2006/0229592 A1 | | 10/2006 | Yokoi et al. | |
| 2007/0106175 A1 | | 5/2007 | Uchiyama et al. | |
| 2007/0270651 A1 | | 11/2007 | Gilad et al. | |
| 2008/0200757 A1 | | 8/2008 | Glukhovsky | |
| 2010/0137686 A1 | | 6/2010 | Meron | |

FOREIGN PATENT DOCUMENTS

| | | |
|---|---|---|
| JP | 57-45833 | 3/1982 |
| JP | 58-10067 | 1/1983 |
| JP | 63-070820 | 3/1988 |
| JP | 63-226615 | 9/1988 |
| JP | 3-289779 | 12/1991 |
| JP | 04-008341 | 1/1992 |
| JP | 4109927 | 4/1992 |
| JP | 1992-144533 | 5/1992 |
| JP | 4-180736 | 6/1992 |
| JP | 5015515 | 1/1993 |
| JP | 06-114036 | 4/1994 |
| JP | 6142081 | 5/1994 |
| JP | 7289504 | 11/1995 |
| JP | 08-126627 | 5/1996 |
| JP | 09327447 A | 12/1997 |
| JP | 10-65131 | 3/1998 |
| JP | 2001-112740 | 4/2001 |
| JP | 2001-170002 | 6/2001 |
| JP | 2001224553 | 8/2001 |
| JP | 2003-093367 | 4/2003 |
| WO | WO 92/21307 | 12/1992 |
| WO | WO 98/11816 | 3/1998 |
| WO | WO 01/08548 | 2/2001 |
| WO | WO 01/50941 | 7/2001 |
| WO | WO 01/53792 | 7/2001 |
| WO | WO 01/65995 | 9/2001 |
| WO | WO 01/87377 | 11/2001 |

(56) References Cited

FOREIGN PATENT DOCUMENTS

| WO | WO 02/26103 | 4/2002 |
|----|----|----|
| WO | WO 02/080376 | 10/2002 |
| WO | PCT/IL2003/000785 | 9/2003 |
| WO | WO 2004/028336 | 4/2004 |
| WO | WO 2004/058041 | 7/2004 |

OTHER PUBLICATIONS

U.S. Appl. No. 11/802,121, filed May 21, 2007, Gilad et al.
International Search Report for PCT/IL2003/001104 dated Oct. 1, 2004.
The Radio Pill, Rowlands, et al., British Communications and Electronics, Aug. 1960, pp. 598-601.
"Video Camera to Take"—RF Systems Lab.
Wellesley company sends body montiors into space—Crum, Apr. 1998.
Wireless transmission of a color television moving image from the stomach using a miniature CCD camera, light source and microwave transmitter. Swain CP, Gong F, Mills TN. Gastrointest Endosc 1997;45:AB40.
PCT International Search Report of International Application No. PCT/IL01/00912.
BBC News Online—Pill camera to 'broadcast from the gut', Feb. 21, 2000, www.news.bbc.co.uk.
Office Action for U.S. Appl. No. 09/963,950 mailed Sep. 29, 2003.
Office Action for U.S. Appl. No. 09/963,950 mailed Apr. 8, 2004.
Office Action for U.S. Appl. No. 09/963,950 mailed Jan. 26, 2005.
U.S. Appl. No. 12/159,745, filed Dec. 22, 2008, Betesh, Ido.
Office Action for U.S. Appl. No. 09/963,950, dated Jan. 26, 2005.
Office Action for U.S. Appl. No. 09/963,950, dated Sep. 29, 2003.
Office Action for U.S. Appl. No. 09/963,950, dated Oct. 22, 2003.
Final Office Action for U.S. Appl. No. 09/963,950, dated Apr. 8, 2004.
www.rfnorika.com—Norika v3, Dec. 24, 2001.
"Robots for the future"—Shin-ichi, et al. Nov. 29, 2001.
Office Action of U.S. Appl. No. 10/482,218 dated Jun. 6, 2006.
Office Action of U.S. Appl. No. 11/892,815 dated Sep. 25, 2009.
Office Action of U.S. Appl. No. 10/482,218 dated Jan. 25, 2006.
Office Action of U.S. Appl. No. 10/482,218 dated Feb. 26, 2007.
Office Action of U.S. Appl. No. 10/540,890 dated Jan. 19, 2010.
Office Action issued on Jul. 1, 2009 in U.S. Appl. No. 10/540,890.
Office Action of U.S. Appl. No. 11/802,121, dated Dec. 1, 2009.
U.S. Appl. No. 60/801,385, filed May 19, 2006, Gilad et al.
Final Office Action, issued Jan. 19, 2010, for U.S. Appl. No. 10/540,890.
Office Action, issued Nov. 25, 2005, for U.S. Appl. No. 10/423,023.
Final Office Action, issued Jul. 12, 2006, for U.S. Appl. No. 10/423,023.
Office Action, issued Mar. 29, 2007, for U.S. Appl. No. 10/423,023.
Final Office Action, issued Dec. 11, 2007, for U.S. Appl. No. 10/423,023.
Office Action, issued Dec. 31, 2008, for U.S. Appl. No. 10/423,023.
Final Office Action, issued Aug. 4, 2009, for U.S. Appl. No. 10/423,023.
Final Office Action, issued May 24, 2010, for U.S. Appl. No. 11/802,121.
Notice of Allowance, issued Aug. 23, 2010, for U.S. Appl. No. 10/540,890.
Final Office Action issued for U.S. Appl. No. 12/700,596 and dated Nov. 17, 2011.
Office Action issued by the United States Patent and Trademark Office for U.S. Appl. No. 11/802,121 dated Feb. 12, 2013.
Office Action issued for U.S. Appl. No. 12/700,596 and dated Apr. 4, 2011.
Office Action, issued Apr. 4, 2011, for U.S. Appl. No. 12/700,596.
Notice of Allowance, mailed Jan. 4, 2011, for U.S. Appl. No. 10/540,890.

* cited by examiner

IMMOBILIZABLE IN-VIVO IMAGER WITH MOVEABLE FOCUSING MECHANISM

RELATED APPLICATION DATA

This application claims benefit from U.S. provisional application Ser. No. 60/533,264, filed on Dec. 31, 2003, entitled AN IMMOBILIZABLE IN-VIVO IMAGER WITH MOVEABLE FOCUSING MECHANISM which is incorporated in its entirety by reference herein.

FIELD OF THE INVENTION

The present invention relates to in-vivo sensing devices. More specifically, the present invention relates to a device, system and method for monitoring an in-vivo site, for example, for post surgery monitoring, and possibly focusing an image of an in vivo site on an imager.

BACKGROUND OF THE INVENTION

In-vivo sensing devices, such as thermometers, pH meters, optical scanners, image sensors and so on, can be used for unobtrusively monitoring bodily systems. Some in-vivo sensors move through body lumens and can be remotely controlled. However, it is sometimes desirable to immobilize a sensing device in-vivo for continuous imaging of an in-vivo site, for example, for post surgery monitoring.

In the time immediately after surgery patients frequently experience organ functional problems. For example, during surgery in the gastrointestinal tract (GI) the blood pressure at the vicinity of the surgical site is reduced and peristalsis is arrested. After surgery the blood pressure increases and peristalsis is resumed sometimes causing bleeding from the surgical site into the intestinal lumen.

Also, for example, in treating coronary artery disease, it is sometimes necessary to bypass coronary arteries with a vascular graft, which is surgically attached to the heart, to circumvent a blocked coronary artery. After surgery, cardiac functional problems may occur due to build-up of stenotic lesions or other obstructions to the flow of blood through the implanted graft.

Postoperative monitoring of the gastrointestinal tract is important to avoid allowing too much time to elapse before blood loss into the intestine is detected.

Similarly, it is important that the condition of a vascular graft be monitored, post-surgery, to detect the further build-up of stenotic lesions or other obstructions to the flow of blood through the implanted graft.

Various catheterization procedures are known for assessing the flow characteristics of a blood vessel or blood vessel graft. However, the introduction of catheters into the vascular system may result in damage to blood vessels.

One prior art system describes an implantable system for monitoring blood flow through surgically implanted grafts. The system, which may include Doppler crystal transducers, utilizes a subcutaneously implanted electrical plug-type connector, accessible through an incision at the implant site, and electrical conductors to connect terminals on that plug to the Doppler crystal transducers.

Ultrasound echo imaging is known for visualization and examination of a patient's heart However, methods of echocardiography do not always result in good quality images after cardiac surgery.

Monitoring or imaging in-vivo processes, not necessarily related to post surgical events, may also be an important diagnostic tool. For example, in endometriosis, in which cells that normally grow inside the uterus instead grow outside the uterus. Endometrial cells line the uterus and are normally shed each month during menstruation. When endometrial cells grow outside the uterus, the cells may implant. These implants occur commonly within the fallopian tubes and on the outside of the tubes and ovaries, the outer surface of the uterus and intestines and anywhere on the surface of the pelvic cavity. They can also be found, less often, on the surface of the liver, in old surgery scars or, very rarely, in the lung or brain. The implants cause internal bleeding, which leads to tissue inflammation and later, scarring and possibly infertility. Endometriosis can be suspected based on symptoms of pelvic pain and findings during physical examinations in the doctor's office but neither the symptoms nor the physical examination can be relied upon to establish the diagnosis of endometriosis. Imaging studies, such as ultrasound, can be helpful in studying the pelvis, but still cannot accurately diagnose endometriosis. Direct visual inspection and tissue biopsy of the implants are necessary for accurate diagnosis. Currently, the only accurate way of diagnosing endometriosis is at the time of surgery (either by open standard laparotomy or laparoscopy).

Monitoring an in-vivo site by way of, for example, imaging over a sustained period of hours or days may be beneficial.

SUMMARY OF THE INVENTION

Embodiments of the invention describe a system and method for monitoring a site in-vivo. According to some embodiments the system includes a housing configured for being immobilized in-vivo; and an imaging device connected to or included within such housing (directly or indirectly, e.g., via other elements), where such imaging device includes a moveable or otherwise adjustable focusing mechanism.

Embodiments of the invention also describe a method of imaging an in-vivo site. According to some embodiments the method includes immobilizing a housing on an in-vivo surface and focusing an imaging device attached to such housing onto an in-vivo site to be imaged.

Further embodiments of the invention describe an autonomous in-vivo device that may be capable of passing through a body lumen. Such device may include a housing configured for being temporarily immobilized in-vivo and an imaging device connected to such housing, such imaging device having a typically moveable focusing mechanism.

BRIEF DESCRIPTION OF THE FIGURES

The present invention will be understood and appreciated more fully from the following detailed description taken in conjunction with the figures in which.

Figure 1:
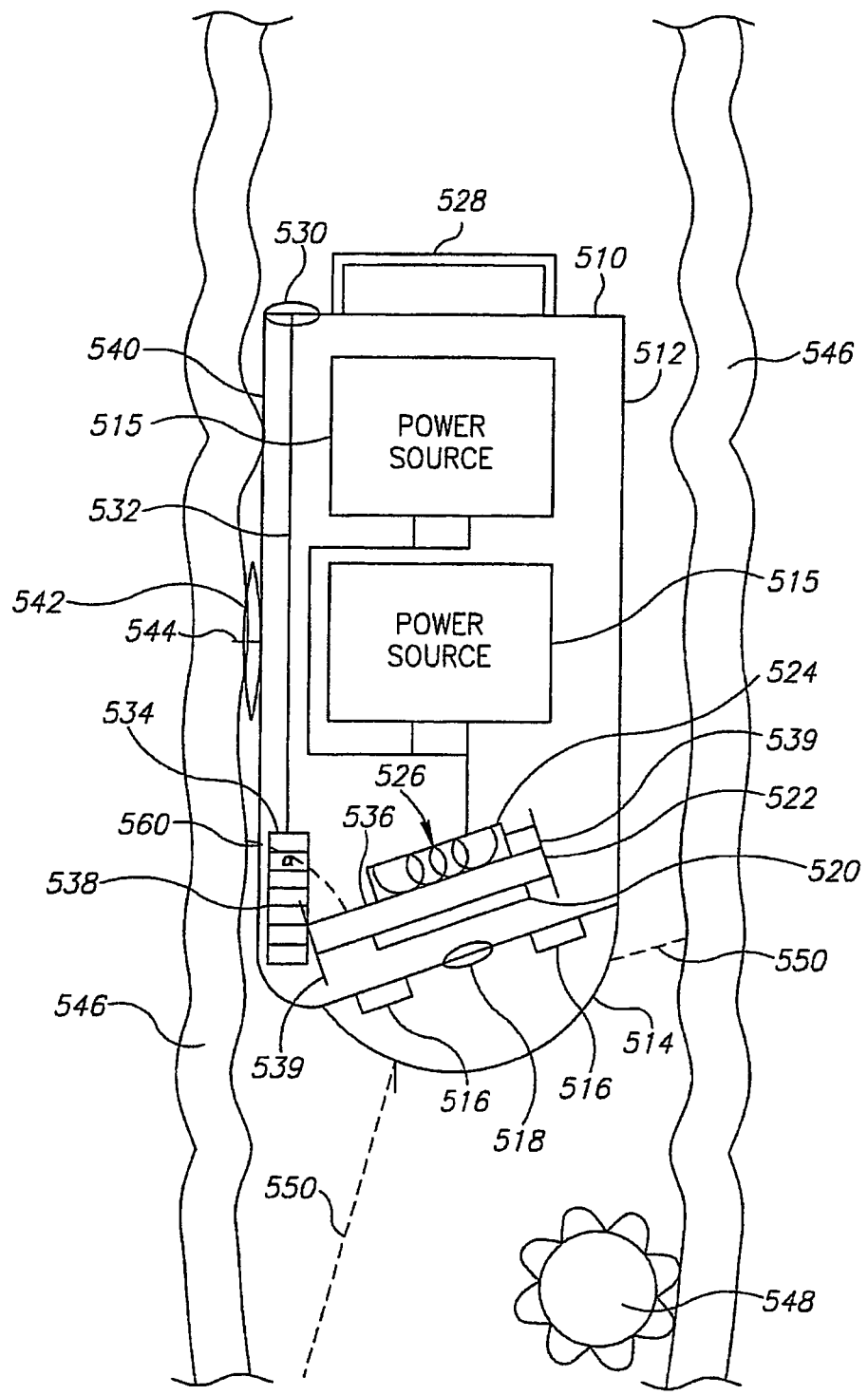
FIG. 1 is a schematic illustration of components of an immobilizable imaging device with a moveable focusing mechanism in accordance with an embodiment of the invention.

It will be appreciated that for simplicity and clarity of illustration, elements shown in the figures have not necessarily been drawn to scale. For example, the dimensions of some of the elements may be exaggerated relative to other elements for purposes of clarity.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

According to an embodiment of the present invention there is provided a device, system and method for immobilizing, affixing or adhering an in-vivo sensing device including for example an imager to an in-vivo site and focusing such imager on a site to be monitored.

According to some embodiments of the present invention the system may include a sensing device, a transmitter that transmits the output of the sensing device, a reception system for receiving the transmitted output and a power source, which provides power to the elements of the system. According to one embodiment, the sensing device may be connected to or included within a housing (directly or indirectly, e.g., via other elements), which is configured for being transiently or temporarily immobilized in the vicinity of a surgical site. The sensing device may be any device that is adapted for being placed in-vivo (for example, along the GI tract) that may sense environment conditions such as the presence of blood, pH, temperature, electrical impedance of tissues etc., and that may transmit (such as by radio) output relating to changes in the environment conditions. According to one embodiment the sensor may be disposed within the housing.

The invention may be utilized for monitoring in-vivo sites in diverse body systems, as will be exemplified herein. In one embodiment there is provided a system for monitoring a site in the GI tract, in which the sensing device is an imaging system. The imaging system may typically include at least one illumination source such as a white LED (light emitting diode) and/or an OLED (Organic LED) and an imaging device such as a CCD or CMOS image sensor. The imaging system may further include an optical system for imaging an area of interest onto the imaging system. The optical system may include mirrors and/or lenses for collimating the light from the illumination source and/or light reflected from an in vivo site onto the imaging device. In accordance with this embodiment a reception system may receive for example a transmitted video output and may include an antenna array capable of surrounding a body for receiving the transmitted video output and for producing a plurality of received signals and/or a demodulator capable of transforming the plurality of received video signals into, for example a single video data stream. Optionally the reception system may include a display, such as an LCD, for displaying the data (e.g., image data) transmitted to it.

The system and method of the present invention may be used with or in an imaging system such as that described in International Publication Number WO 01/65995, entitled "A Device and System for In-Vivo Imaging", international publication date Sep. 13, 2001, international filing date Mar. 8, 2001. A further example of an imaging system with which the system and method of the present invention may be used is described in U.S. Pat. No. 5,604,531 to Iddan et al., entitled "In-Vivo Video Camera System", filed on Jan. 17, 1995, and in U.S. patent application Ser. No. 09/800,470. Both of these publications are assigned to the common assignee of the present application and are hereby incorporated by reference.

According to embodiments of the present invention a sensing system, for example an imaging system may provide direct visual information of the in-vivo site (e.g., a surgical site) such that visibly detectable changes at the site, such as bleeding, swelling etc. can be seen by an external operator. The imaging system may further include a detector coupled to the imaging device that may be optically changed in response to changes in environmental conditions. According to some embodiments the optical change in the detector is imaged and transmitted to a receiving system and may be shown on a display of the receiving unit to alert an external operator of the changed conditions. For example, the imaging system may comprise a pH meter that undergoes a color change in response to pH changes in its vicinity. According to some embodiments, the imaging system may include a detector of chemical substances, such as blood components, which undergoes a change in color in response to the presence of the chemical substances. In both cases a change in color will be detected by the imaging device and will be transmitted and received by the reception system for the inspection of an external operator.

According to embodiments of the present invention, the sensing device, such as an imaging system, may further be in communication with a processor/control for analyzing the data detected by it and possibly for controlling the sensing device. For example, images of a surgical site may be transmitted to a processor where they are analyzed for the presence and possibly the concentration of blood (by detecting certain changes in color). The image may then be received by the external operator including additional information, generated by the processor, regarding the bleeding at the surgical site. Further, the system may include devices for alerting the external operator. The devices for alerting the external operator may be in communication with the processor. Thus, when the presence of blood is detected by the processor a signal, such as a flashing light or an alarm may be activated to alert the external operator.

The device may be a capsule possibly designed to passively transverse the GI tract. The device may be or may include an autonomous swallowable capsule, but the device may have other shapes and need not be swallowable or autonomous. Embodiments of the device are typically autonomous, and are typically self-contained. For example, the device may be a capsule or other unit where all the components are substantially contained within a container or shell, and where the capsule does not require any wires or cables to, for example, receive power or transmit information. The capsule may comprise a capsule body, which may include an optical window, behind which are positioned illumination sources and an imaging device. According to some embodiments the capsule body may house additional elements of the system, such as a processor/controller for processing image data obtained by the imaging device and possibly for controlling imaging device, a transmitter for transmitting images of the surgical site to an external reception system and a power source, such as a battery.

An imaging system, for example, an immobilizable imaging system according to an embodiment of the invention may be used with or in an imaging system such as that described in International Publication Number WO 02/26103 entitled "System and Method for Post Surgical Monitoring", assigned to the common assignee of the present application and incorporated herein by reference.

According to some embodiments of the present invention, the system and method of the invention may enable post surgical monitoring in the GI tract without having to leave an opening in the patient's body or having to cut the patient a second time in order to retrieve the monitoring system.

Monitoring a site of drainage in accordance with this embodiment of the invention enables an external operator to easily see, without using external techniques such as CT, if the site has been drained, to see that there is no active bleeding at the site, etc., or if there is leaking, to identify the site of leaking.

Further, in accordance with an embodiment of the invention an imaging system as described herein may be immobilized in-vivo for monitoring in-vivo processes. For example, an immobilizable imaging system according to an embodiment of the invention may be immobilized in a uterus for monitoring the uterus environment, for example, the development of a fetus in that uterus. The imaging system, which may be battery powered and which may wirelessly transmit images to an external recording system, may be programmed to obtain images of the fetus at predetermined intervals, such as once every 24 hours. According to one embodiment, images of the fetus may provide devices for visually monitoring the development of a fetus and, at the same time, may ensure a long life of the battery so as to enable imaging over a long period (e.g., the term of pregnancy). Alternatively, the imaging system may be externally induced, as known in the art. In addition to continuous monitoring of the development of the fetus, real time images may be obtained when required, for example, when the patient is visiting the doctor or when the patient is experiencing difficulties and visual sight of the fetus may provide an explanation for the experienced difficulties.

An immobilizable imaging system according to an embodiment of the invention may also be used for diagnosing and/or monitoring in-vivo procedures such as endometriosis. An immobilizable imaging system according to an embodiment of the invention can be immobilized at sites of endometrial implants or of suspected implants, such as within the fallopian tubes, and transmit images of the site to an external receiving system for detecting or monitoring endometrial implants.

Also, an immobilizable imaging system according to an embodiment of the invention can be immobilized in a blood vessel, for example, for monitoring restinosis after implantation of a stent. The imaging system can be immobilized at the site of the stent implantation and images of the site can be obtained, as above, at predetermined intervals, for example, once a week. According to one embodiment, images of the site of the stent implantation, may provide devices for warning a physician of the occurrence of restinosis or any other pathologies related to the stent.

In another embodiment of the invention the housing may include an imaging system, for example, as described herein, and may further comprises a detector of substances in an in-vivo environment, such as blood, sugar, amino acids, microorganisms etc, or of conditions prevalent in an in-vivo environment, such as pH, temperature etc. The detector, which may be adhered to the housing in such a way that it is included in the angle of view of the imaging system, may react to the presence of substances or environmental conditions by causing, for example an optical change. An example of such a detector may be a strip of pH sensitive material that is adhered to the optical window of the imaging system. Other examples are described in WO 01/53792, which is assigned to the common assignee of the present invention and which is hereby incorporated by reference. A device according to this embodiment, which is immobilized at an in-vivo site, may provide an external operator with images of the in-vivo site and simultaneously with information relating to the environmental conditions at the in-vivo site.

Reference is made to FIG. 1, a schematic illustration of components of an immobilizable imaging device with a moveable or otherwise adjustable focusing mechanism in accordance with an embodiment of the invention. Device 510 may include a container, housing or body 512 which may include for example an optical dome e.g. window 514, behind or adjacent to which may be positioned illumination sources 516, a lens 518, an imaging sensor 520, a controller or processor 522, a transmitter 524 and one or more power sources 515, such as for example batteries. Transmitter 524 may include one or more antennas 526 or antenna arrays that may be suitable for example for transmitting data such as for example image data to an external receiver or recorder. Processor 522 may control various components of device 510 and may be capable for example of varying parameters, such as intensity or duty cycle of illumination produced by illumination sources 516 or a frame rate or rate of image capture by imaging sensor 520.

A system and method for varying parameters, such as frame rate is described for example in embodiments of U.S. application Ser. No. 09/571,326 entitled "System for Controlling In vivo Camera Frame Capture and Frame Display Rates", which is assigned to the common assignee of the present invention and hereby incorporated by reference. In some embodiments, power may be supplied to device 510 through an external source, e.g., a transdermal wireless power supply system that may supply power to device 510 from a source external to a body. In some embodiments, device 510 may include a receiver that may receive a signal from a source external to a body, and such signal may activate or alter a functional state of device 510.

Device 510 may include a handle or endoscope dock 528 by which an endoscope, laparoscope or other suitable device may releasably hold device 510 while device 510 is inserted or maneuvered into position in an in-vivo site.

Device 510 may include a focusing pivot, knob, button or lever 530, by which for example an external operator may focus images onto imaging sensor 520 from outside of device 510 or outside of a body. Focusing lever 530 may in some embodiments be connected to focusing shaft 532 which may for example be further connected to focusing screw 534. According to some embodiments, a screw need not be used. Another, possibly different shaped focusing element may be used. An end or base 536 of imaging sensor 520 or of for example a platform or base to which imaging sensor 520 may be attached, may be moveably or slideably in contact with a thread 538 of focusing screw 534. A side 540 such as for example a back of device 510 may include a fastener or immobilizing unit such as for example a vacuum pad 542 and pin 544 which may immobilize device 510 against an endolumenal wall 546. Other suitable components or series of components may be used for adjusting a focusing system.

Device 510 may be box-like in shape, spherical, cylindrical or may be shaped in other fashions as may be suitable for placement, positioning or movement in-vivo and as may be suitable for angling imaging sensor 520 towards an area to be monitored. In some embodiments, device 510 may be an autonomous imaging device with a capsule-like shape.

In some embodiments, processor 522 may vary the intensity or frequency of illumination produced by illumination sources 516 to, for example, match the depth of field of the image to be captured by image sensor 520. A system and method for varying illumination is described for example in embodiments of U.S. patent application Ser. No. 10/202,608 filed Jul. 25, 2002 and entitled "Apparatus and Method for Controlling Illumination in an In-vivo Imaging Device", hereby incorporated by reference. According to some embodiments illumination and/or other parameters of the device 510 may be controlled by other components. For example, control of such parameters may be integral to the image sensor 520. Other suitable illumination varying systems and methods may be used. In some embodiments it may not be necessary to match the illumination of illuminating devices 516 to the depth of field or other aspects of an area to be monitored or the imaged to be captured.

In operation, device 510 may be inserted into a body lumen such as, for example, esophagus, stomach, intestine or other area of the GI tract. In some embodiments, device 510 may be inserted during a surgical procedure for example when a body lumen is open. In some embodiments, device 510 may be attached to for example, an endoscope or other instrument and maneuvered into position from outside of a body. An endoscope, laparoscope or other instrument may in some embodiments hold or grasp device 510 by way of for example dock 528 or by way of a handle attached to for example an end of device 510. The endoscope or other instrument may release dock 528 when for example device 510 had been immobilized into position or at other suitable times. Other methods of releasably grasping or holding device 510 on an endoscope may be used such as for example, by way of an electromagnet, a suction cup, detachable adhesive, mechanical fitting, hydraulic fitting etc., which may facilitate holding device 510 during its insertion into a body lumen and releasing device 510 once it has been inserted or immobilized in a body lumen.

Device 510 may be placed or maneuvered into position so that for example an item or area to be monitored 548 is within the viewing area boundaries 550 of imaging sensor 520. As so positioned, device 510 may be affixed or immobilized against or on an endo-lumenal wall 546 such that device 510 remains fixed in a given position and such that imaging sensor 520 may monitor or capture images of an area or configuration 548 to be monitored.

In some embodiments an immobilizing unit that may hold device 510 in position on for example an endo-lumenal wall 546 may include a vacuum pad 542 and pin 544. An external operator of an endoscope may press or maneuver a side 540 of device 510 into contact with endo-lumenal wall 546 thereby compressing vacuum pad 542 against such wall 546 and establishing a vacuum bond that may hold, affix or immobilize device 510 in place on the endo-lumenal wall 546. In some embodiments, an anchor, screw or pin 544, may be fitted into vacuum pad 542. According to one embodiment of the present invention, when side 540 of device 510 is pressed onto endo-lumenal wall 546, pin 544 may embed in endo-lumenal wall 546 further securing the bond between device 510 and endo-lumenal wall 546. In some embodiments, pin 544 may be made of a material that may degrade or dissolve over time upon exposure to for example the moisture of an in-vivo environment such as for example a GI tract. Suitable materials for pin 544 may include for example caramel, bio-degradable plastic resins or starches such as gelatin or wax. According to embodiments of the present invention, after a period of time, vacuum pad 542 may release itself from endo-lumenal wall 546 and pin 544 may dissolve, thereby releasing device 510 from its affixed position. In some embodiments, the released device 510 may move through and possibly out of a body lumen propelled for example by peristalsis, or may be removed surgically or by endoscope.

In some embodiments, imaging sensor 520, lens 518 or other component of device 510 may be moved or adjusted to focus the images of area or configuration to be monitored 548 that are captured by device 510. In some embodiments, an external operator may use an endoscope such as for example the one by which device 510 is held during insertion into a body lumen, for example to rotate or otherwise adjust focusing lever 530 from the outside of a body lumen. According to one embodiment of the present invention, focusing lever 530 may be configured for example in the shape of a head of a screw, button or knob. According to some embodiments, an end of an endoscope may include a shaft that may, for example rotate, compress, force or otherwise adjust focusing lever 530 upon command by an external operator through the endoscope.

In some embodiments, focusing lever 530 may connect to shaft 532 and further to focusing screw 534 such that lever 530 rotates, compresses or otherwise adjusts screw 534. An edge, point or threading on base 536 of for example imaging sensor 520, or a platform to which imaging sensor 520 may be attached, may be moveably joined onto a thread 538 of screw 534 such that when screw 534 is rotated, compressed or otherwise adjusted, base 536 may move closer to or further away from lens 518, thereby moving for example imaging sensor 520 and focusing the image captured by imaging sensor 520. The position of one or more lenses relative to an imager may thus be adjusted. In some embodiments, one or more ends of base 536 may move within a track, indentation or groove 539 in for example an inside wall of body 512, as imaging sensor 520 is moved closer to or further away from lens 518. Other methods of moving imaging sensor 520 are possible, such as by compressing a shaft 532 to move base 536.

In some embodiments, device 510 may be constructed so that some or all of window 514, imaging sensor 520 and base 536 may be at an acute angle 560 to endo-lumenal wall 546 to which device 510 may be attached. For example, imaging sensor 520 may be positioned at a non-ninety degree angle to a substantially longitudinal axis X of an oblong device 510 (device 510 may have other shapes, such as spherical), or at a non-ninety degree angle to the plane of the in-vivo surface on which it is mounted. At such angle, there may be included within viewing area boundaries 550, an area to be monitored for example area or configuration 548 that is on for example an endo-lumenal wall which is, for example, opposed to wall 546 to which device 510 may be attached. Other non-acute angles may be used. In some embodiments, the angle of an imaging device may be adjusted by an external operator.

In some embodiments an external operator may view images captured by device 510 on an external receiving and display system. An external operator may (for example before releasing device 510 from an endoscope) focus the image viewed on such display system by rotating or compressing focusing lever 530 and adjusting the distance between image sensor 520 and lens 518.

Figure 2:
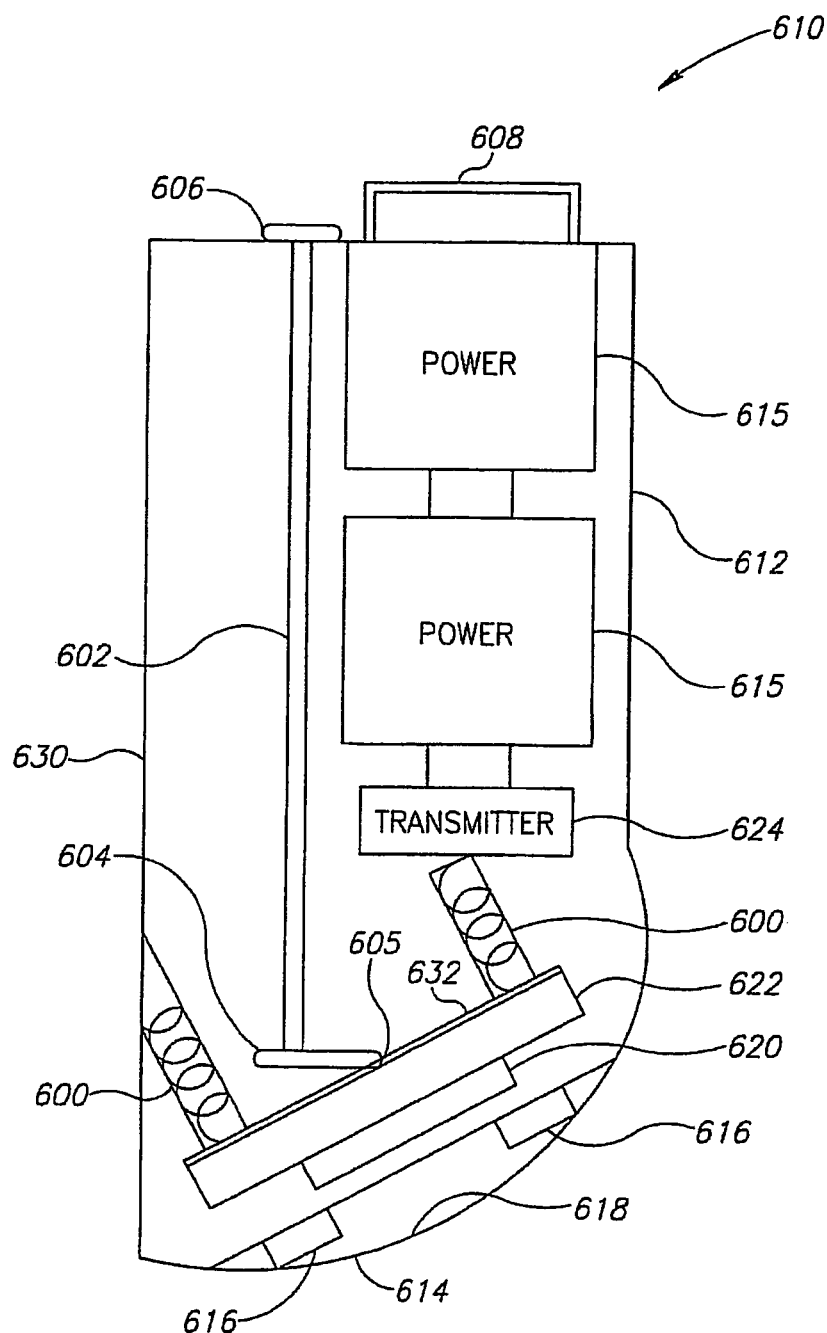
FIG. 2 is a schematic illustration of components of an immobilizable imaging device with a moveable focusing mechanism using a spring in accordance with an embodiment of the invention.

FIG. 2 is a schematic illustration of components of an immobilizable imaging device with a focusing mechanism using a spring, in accordance with an embodiment of the invention. According to one embodiment of the present invention, device 610 may include a housing or body 612 which may include for example an optical dome, e.g. window 614, behind or adjacent to which may be positioned illumination sources 616, and/or lens 618, and/or imaging sensor 620, and/or controller and/or processor 622, and/or transmitter 624 and/or one or more power sources 615, such as for example batteries. According to one embodiment of the present invention, device 610 may include a dock 608 or a handle by which device 610 may be releasably grasped or held by, for example an endoscope, during insertion into a body lumen. According to some embodiments of the present invention, device 610 may include a focusing control or button 606, such as for example a rotatable, compressible or otherwise adjustable knob or screw which may be rotated, compressed or adjusted by for example an external operator by way of for example an endoscope. According to some embodiments button 606 may be electrically connected to a typically electrical focusing mechanism. According to some embodiments the focusing mechanism may be a mechanical system. According to one embodiment of the present invention, button 606 may be connected to shaft 602 which may be further connected to cam 604 such that when button 606 is rotated or adjusted, shaft 602 rotates or adjusts the position of cam 604. According to some embodiments, cam 604 may be or include for example a disc or sphere that may be attached to shaft 602 at a point off-center of such disc or sphere of cam 604. In some embodiments, cam 604 may have an oblong, oval or other asymmetrical shape. In some embodiments, cam 604 may be irregularly spherical in shape. In some embodiments, a side edge 605 of cam 604 may be in contact with for example base 632 such that base 632 may press gently on such edge 605 of cam 604. When rotated by shaft 602, the edge 605 of cam 604 that it is contact with base 632 may move asymmetrically as a result of the off center placement of shaft 602 on cam 604 or the oblong or oval shape of cam 604.

Processor 622 may be moveably held by one or more triggered springs 600. Triggered springs 600 may be anchored for example at one end on a wall or shell 630 of body 612 or for example against transmitter 624 or some other internal component of device 610. Another end of spring 600 may be attached to for example a base 632 of for example processor 622 or a platform upon which processor 622 and imaging sensor 620 may be held. According to some embodiments, spring 600 may moveably hold base 632 such that when spring 600 is extended, base 632 and imaging sensor 620 may move forward towards lens 618, and when spring 600 may be compressed, base 632 and imaging sensor 620 may move away from lens 618.

According to some embodiments of the present invention, in operation, the asymmetrical movement during rotation of edge 605 of cam 604 against base 632, may in some phases of the rotation of cam 604 push base 632 and image sensor 620 towards lens 618. The force of edge 605 against base 632 may extend spring 600 as base 632 moves forward toward lens 618. In another phase of the rotation of cam 604, edge 605 may allow base 632, as pulled by spring 600, to be drawn back away from the direction of lens 618. The various phases of the rotation of cam 604 may move base 632 and image sensor 620 either towards of away from lens 618. According to some embodiments of the present invention, an external operator rotating button 606 by way of for example an endoscope may focus the images captured by image sensor 620.

Figure 3:
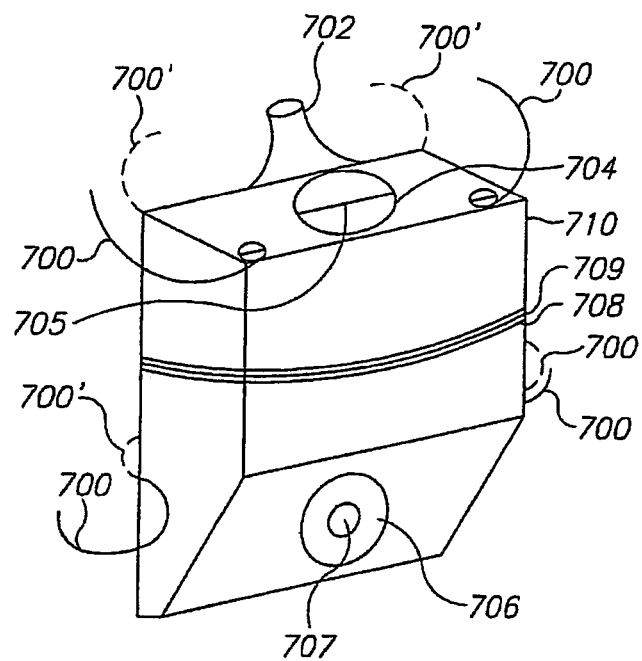
FIG. 3 is a schematic illustration of an in-vivo immobilizable device according to further embodiments of the invention.

Reference is made to FIG. 3, a schematic illustration of an in-vivo immobilizable device according to further embodiments of the invention According to one embodiment of the present invention, device 710 may include a container, housing or body which may include for example a window 706, a lens 707, and a dock 704 by which for example device 710 may be held or grasped by for example an endoscope. According to some embodiments of the present invention, device 710 may be or include an in-vivo sensor such as an imager and may include an image sensor, illumination sources, power source, transmitter and other components. Device 710 may include one or more immobilizing units that may hold or secure device 710 to an, for example endo-lumenal surface According to some embodiments, such immobilizing units may be or include for example one or more rotatable clasps 700 a gluing tube, vacuum pads, etc. for example, as discussed herein. Rotatable clasps 700 may swing or rotate out from a side or corner of device 710 to assume a closed position indicated by dashed lines 700' in FIG. 3. When rotated into a closed position, clasps 700 may pinch or grab for example an end lumenal tissue or wall that is proximate to device 710, and may hold device 710 securely next to such wall. In such position, an imager behind dome 707 may capture images of an area to be monitored.

In some embodiments, clasps 700 may be configured in opposing pairs that may rotate towards each other thereby pinching a tissue between them. Other configurations of clasps may be used. In some embodiments a lever 705 in dock 704 may be rotated by way of for example an endoscope by an external operator Other methods of moving or closing clasps 700 are possible. According to some embodiments, lever 705 may be connected to one or more gears in device 710, and may rotate one or more clasps 700 into an open or closed position. Other suitable methods of connecting lever 705 to clasps are possible. In some embodiments, clasps 700 may be made of a degradable material that may dissolve over time on exposure to a moist in-vivo environment. Once clasps 700 degrade, device 710 may be freed to possibly pass through or out of a body lumen such as for example by peristalsis through a GI tract.

In some embodiments, device 710 may include a bladder or tube 702 in which glue or an adhesive may be held and released to stick a back or side of device 710 to an endo-lumenal wall. In some embodiments glue or an adhesive may be stored in tube 702 and released when bladder or tube 702 is punctured by for example a force exerted from an endoscope. In some embodiments, a glue or adhesive may be applied by injecting glue through a tube or pipe in an endoscope onto a side of device 710 that is proximate or in contact with an endo-lumenal wall. Glue or adhesive may bond device 710 to the endo-lumenal wall such that device 710 may monitor or capture images of an area to be monitored. In some embodiments, glue or adhesive may be degradable over time in an in-vivo environment, such that over time device 710 may be freed of the endo-lumenal wall to which it was stuck and may pass through or out of a body lumen. Suitable glues may include cyanoacrylates and other similar compounds as may be suitable for in-vivo gluing.

In some embodiments, device 710 may include an indentation or channel 708 that may for example pass around a circumference of device 710, and which may accept or in which may be held a suture 709 that may be sewn into an endo-lumenal wall and around device 710. A suture 709 may hold device 710 in place so that device 710 may monitor or collect images of an area to be monitored. In some embodiments, suture 709 may be degradable over time in an in-vivo environment, such that over time device 710 may be freed of the endo-lumenal wall to which it was sewn and may pass through or out of a body lumen.

Figure 4:
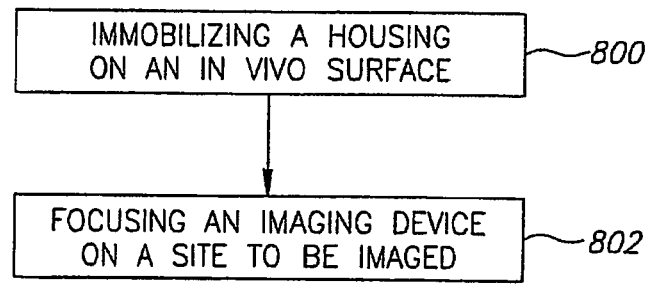
FIG. 4 is a flow chart diagram of a method in accordance with an embodiment of the invention.

Reference is made to FIG. 4, a flow chart of a method in accordance with an embodiment of the invention. In block 800 a housing containing for example an imaging device may be immobilized on or against an endo-lumenal wall or other in-vivo surface. The device may include an imaging sensor or other monitor capable of monitoring an in-vivo area to be monitored and an immobilization unit such as for example rotatable clasps, a suture through a channel, a glue tube, vacuum pad, pin, screw, etc.

In some embodiments, a housing of a device may be positioned or secured against an endo-lumenal surface so that an imaging sensor of the device is at an acute angle relative to an endo lumenal wall against which such housing is immobilized. Such positioning may enable the image sensor to capture images of an area to be monitored that is for example on an opposing endo-lumenal wall from such point of immobilization.

In block 802, an imaging device or optical system of a device may be focused on a site or in-vivo area to be monitored. Focusing may be performed for example by an external operator by way of for example an endoscope. A focusing mechanism may be adjusted or moved. An imaging device may include a focusing mechanism in the form of for example a cam or screw that may be rotated, compressed or otherwise adjusted to alter the position of an imaging sensor relative to the position of a lens, or to otherwise increase or decrease the distance between an imaging sensor and a lens, to focus the image.

It will be appreciated by persons skilled in the art that the present invention is not limited by what has been particularly shown and described herein above. Rather the scope of the invention is defined by the claims which follow:

I claim:

1. An autonomous in-vivo device for monitoring a site in-vivo, the in-vivo device comprising:
    a housing adapted to be mountable to an in-vivo surface for being immobilized in-vivo, the housing comprising:
    a dome-shaped optical window;
    an optical system positioned behind the optical window, the optical system comprising a focusing lens;
    an image sensor positioned behind the optical window and within the housing, wherein said image sensor is positioned to face in a direction at an acute angle relative to a side of the housing which is mounted, wherein the angle is adjustable; and
    a moveable focusing mechanism, comprising a focusing lever positioned on the housing, allowing the distance of the focusing lens relative to the image sensor to be adjusted by moving the image sensor by a shaft, wherein the focusing lens is located at a fixed distance from the optical window.

2. The in-vivo device as in claim 1, wherein said housing further comprises rotatable clasps.

3. The in-vivo device as in claim 1, comprising an illumination source.

4. The in-vivo device as in claim 3, comprising a controller to control illumination.

5. The in-vivo device as in claim 1, comprising a controller to control a frame rate of said imaging device.

6. The in-vivo device as in claim 1, wherein said housing further comprises a vacuum pad configured to immobilize said housing to an endo-lumenal surface.

7. The in-vivo device as in claim 1, wherein said housing is configured to accept a suture to immobilize said housing to an endo-lumenal surface.

8. The in-vivo device as in claim 1, further comprising a base to which the imaging sensor is attached, the base comprising an edge moveably joined to a thread, wherein the edge moves within a track.

9. An autonomous in-vivo device configured for passing through a body lumen, the device comprising: a housing adapted to be mountable to an in-vivo surface for being temporarily immobilized in-vivo, the housing comprising: a dome-shaped optical window; an optical system comprising a focusing lens behind the optical window; an image sensor positioned behind the optical window and within the housing, wherein said image sensor is positioned to face in a direction at an acute angle relative to a side of the housing which is mounted, wherein the angle is adjustable; and a moveable focusing mechanism, comprising a shaft and focusing screw positioned on the housing, allowing the distance of the focusing lens relative to the image sensor to be adjusted by moving the image sensor by a shaft, wherein the focusing lens is located at a fixed distance from the optical window.

10. The autonomous device as in claim 9, wherein said imaging device is positioned at an acute angle relative to a surface of a body lumen upon which said housing is immobilized.

11. The autonomous device as in claim 9, comprising means for temporarily immobilizing said housing in vivo.

12. An autonomous in-vivo device for monitoring a site in-vivo, the in-vivo device comprising: a housing adapted to be mountable to an in-vivo surface for being immobilized in-vivo, the housing comprising: a dome-shaped optical window; an optical system comprising a focusing lens behind the optical window; an image sensor positioned behind the optical window and within the housing, wherein said image sensor is positioned to face in a direction at an acute angle relative to a side of the housing which is mounted, wherein the angle is adjustable by a moveable focusing mechanism positioned on the housing; and a base to which the imaging sensor is attached, the base comprising an edge moveably joined to a thread, allowing an end of the base to move within a track, wherein the focusing lens is located at a fixed distance from the optical window.

* * * * *